(12) United States Patent
Usui (10) Patent No.: US 12,419,523 B2
(45) Date of Patent: Sep. 23, 2025

(54) SENSOR DEVICE, CATHETER, AND SYSTEM PROVIDED WITH SENSOR DEVICE

(71) Applicant: SEMITEC Corporation, Tokyo (JP)

(72) Inventor: Masayuki Usui, Tokyo (JP)

(73) Assignee: SEMITEC Corporation, Tokyo (JP)

( * ) Notice: Subject to any disclaimer, the term of this patent is extended or adjusted under 35 U.S.C. 154(b) by 1033 days.

(21) Appl. No.: 17/254,846

(22) PCT Filed: Jun. 12, 2019

(86) PCT No.: PCT/JP2019/023241
§ 371 (c)(1),
(2) Date: Dec. 21, 2020

(87) PCT Pub. No.: WO2020/012857
PCT Pub. Date: Jan. 16, 2020

(65) Prior Publication Data
US 2021/0259555 A1   Aug. 26, 2021

(30) Foreign Application Priority Data
Jul. 13, 2018   (JP) .................................. 2018-133051

(51) Int. Cl.
*A61B 5/01*   (2006.01)
*A61B 5/00*   (2006.01)

(52) U.S. Cl.
CPC .............. *A61B 5/01* (2013.01); *A61B 5/0015* (2013.01); *A61B 5/6852* (2013.01);
(Continued)

(58) Field of Classification Search
CPC ......... A61B 5/01; A61B 5/0015; A61B 5/205; A61B 5/6852; A61B 5/6867; A61B 2562/0247; A61B 2562/0271
See application file for complete search history.

(56) References Cited

U.S. PATENT DOCUMENTS

| 2008/0103408 A1* | 5/2008 | Denton | A61B 5/021 600/581 |
| 2010/0056871 A1* | 3/2010 | Govari | A61B 5/06 600/300 |

(Continued)

FOREIGN PATENT DOCUMENTS

| CN | 1395478 | 2/2003 |
| CN | 107072557 | 8/2017 |

(Continued)

OTHER PUBLICATIONS

English translation of PCT/JP2015/067488—published on Jun. 17, 2015 (Year: 2015).*

(Continued)

*Primary Examiner* — Niketa Patel
*Assistant Examiner* — Adreanne A. Arnold
(74) *Attorney, Agent, or Firm* — JCIPRNET (57) ABSTRACT

Provided are a sensor device which can be made small-sized, a catheter, and a system provided with the sensor device. A sensor device (1) is provided with a pipe-shaped distal-end-side member (23), a pressure sensor (4) and a temperature sensor (5) which are integrated and accommodated in an inner space of the distal-end-side member (23), and lead wires (6) connected to the pressure sensor (4) and the temperature sensor (5) and led out to the rear-end side. In the pressure sensor (4) and the temperature sensor (5), sensor elements (41), (51) are formed on one surface side of respective substrates (42), (52) thereof, and are disposed and integrated so that the other-surface sides of the substrates (42), (52) face each other.

14 Claims, 5 Drawing Sheets

(52) U.S. Cl.
CPC .... *A61B 5/6867* (2013.01); *A61B 2562/0247* (2013.01); *A61B 2562/0271* (2013.01); *A61B 2562/12* (2013.01)

(56) References Cited

U.S. PATENT DOCUMENTS

| | | | |
|---|---|---|---|
| 2015/0099942 A1* | 4/2015 | Edouard | A61B 5/0084 600/427 |
| 2018/0116513 A1* | 5/2018 | Bhogu | A61B 5/316 |

FOREIGN PATENT DOCUMENTS

| | | | |
|---|---|---|---|
| CN | 108024729 | 5/2018 | |
| JP | H1133004 | 2/1999 | |
| JP | H1133004 A * | 2/1999 | |
| JP | 2000502275 | 2/2000 | |
| JP | 2001025461 | 1/2001 | |
| JP | 2005507279 | 3/2005 | |
| JP | 2005527079 | 9/2005 | |
| JP | 2007260312 | 10/2007 | |
| JP | 2009523463 | 6/2009 | |
| JP | 2010051801 | 3/2010 | |
| JP | 2016516531 | 6/2016 | |
| JP | 2017536857 | 12/2017 | |
| WO | 2015194598 | 12/2015 | |
| WO | WO-2015194598 A1 * | 12/2015 | A61B 1/00 |
| WO | WO-2017053882 A1 * | 3/2017 | A61B 5/0022 |

OTHER PUBLICATIONS

English translation for JP-H1133004 A, published Feb. 9, 1999. (Year: 1999).*
Office Action of China Counterpart Application, with English translation thereof, issued on Sep. 28, 2023. pp. 1-19.
"International Search Report (Form PCT/ISA/210) of PCT/JP2019/023241," mailed on Sep. 3, 2019, with English translation thereof, pp. 1-4.
Office Action of China Counterpart Application, with English translation thereof, issued on Apr. 23, 2024, pp. 1-19.
"Office Action of China Counterpart Application", issued on Jul. 18, 2024, with English translation thereof, p. 1-p. 12.

* cited by examiner

SENSOR DEVICE, CATHETER, AND SYSTEM PROVIDED WITH SENSOR DEVICE

CROSS-REFERENCE TO RELATED APPLICATION

This application is a 371 application of the International PCT application serial no. PCT/JP2019/023241, filed on Jun. 12, 2019, which claims the priority benefit of Japan Patent Application No. 2018-133051, filed on Jul. 13, 2018. The entirety of each of the above-mentioned patent applications is hereby incorporated by reference herein and made a part of this specification.

TECHNICAL FIELD

The present disclosure relates to a sensor device, a catheter and a system provided with the sensor device.

BACKGROUND ART

Hitherto, for example, in the field of medical equipment, a temperature sensor has been used to measure a deep body temperature, and a pressure sensor has been used to measure a pressure in an abdominal cavity. As a specific example, in a case where a urethra catheter is applied to a patient, a deep body temperature and a bladder internal pressure are measured to monitor biological environment.

A urethra catheter is generally used for the purpose of inserting a catheter into the bladder of a patient from the urethra and continuously discharging urine. In this case, a bladder internal pressure is substantially correlated with an abdominal cavity internal pressure, and thus it is possible to estimate an abdominal cavity internal pressure by monitoring a bladder internal pressure and diagnose pathological conditions such as postoperative complications caused by a rapid increase in the abdominal cavity internal pressure. Further, it is possible to obtain information such as the amount of discharged urine, a respiration rate, a heartbeat, and heartbeat fluctuations by analyzing the bladder internal pressure.

When a deep body temperature and a bladder internal pressure are measured, a method of performing measurement by preparing separate catheters for the deep body temperature (temperature sensor) and the bladder internal pressure (pressure sensor) is used. However, this method is burdensome for a patient, and thus an appropriate method that is less burdensome is required.

On the other hand, attaching both a temperature sensor and a pressure sensor to a distal end portion of a urethra catheter to measure a deep body temperature and a bladder internal pressure at the same time can be considered. However, according to this configuration, an external diameter dimension of the catheter is increased, and a burden on a patient is increased, which results in a problem that practical application is difficult.

CITATION LIST

Patent Literature

[Patent Literature 1]
Japanese Patent Laid-Open No. 2001-25461
[Patent Literature 2]
Published Japanese Translation No. 2000-502275 of the PCT International Publication
[Patent Literature 3]
Published Japanese Translation No. 2009-523463 of the PCT International Publication
[Patent Literature 4]
Published Japanese Translation No. 2017-536857 of the PCT International Publication

SUMMARY OF INVENTION

Technical Problem

The disclosure is contrived in view of the above-described circumstances, and an object thereof is to provide a sensor device that can be made small, a catheter, and a system provided with the sensor device.

Solution to Problem

A sensor device of the present embodiment includes a pipe-shaped distal-end-side member, a pressure sensor and a temperature sensor which are integrated and accommodated in an inner space of the distal-end-side member, and a lead wire which is connected to the pressure sensor and the temperature sensor and is led out to a rear end side. In addition, each of the pressure sensor and the temperature sensor is configured such that a sensor element is formed on one surface side of a substrate of the sensor, and the pressure sensor and the temperature sensor are disposed and integrated so that the other surface sides of the respective substrates face each other.

According to such a configuration, it is possible to provide a sensor device that can be made small. The integration includes, for example, disposition according to simple butting of the other surface sides of the respective substrates and a case according to adhesion of the other surface sides. In other words, the integration is a state where the pressure sensor and the temperature sensor are grouped. The integration is not analyzed in a particularly limited way.

Advantageous Effects of Invention

According to the disclosure, it is possible to provide a sensor device that can be made small, a catheter, and a system provided with the sensor device.

DESCRIPTION OF EMBODIMENTS

Figure 1:
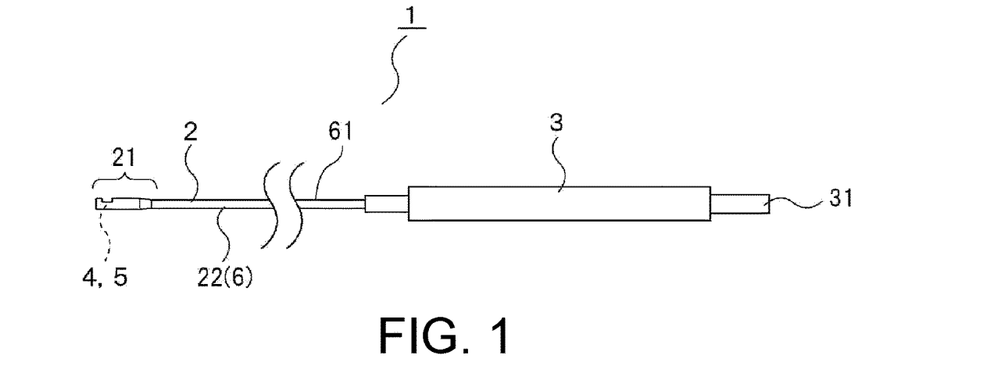
FIG. 1 is a front view illustrating a sensor device according to an embodiment of the disclosure.
Figure 2:
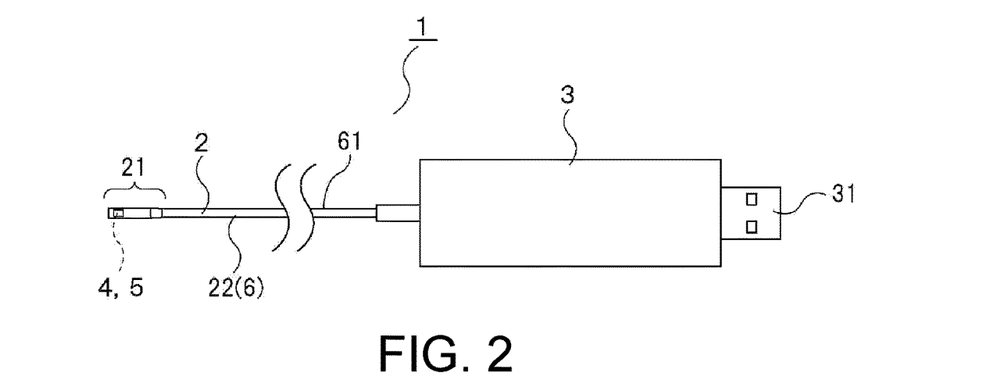
FIG. 2 is a top view illustrating the sensor device.
Figure 3:
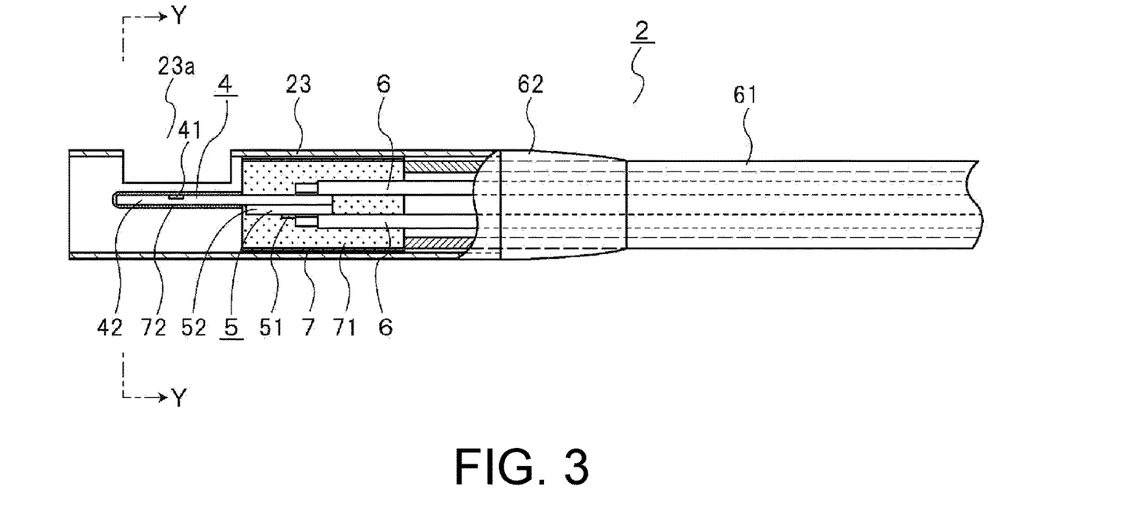
FIG. 3 is a cross-sectional view illustrating a configuration in a distal end portion of the sensor device.
Figure 4:
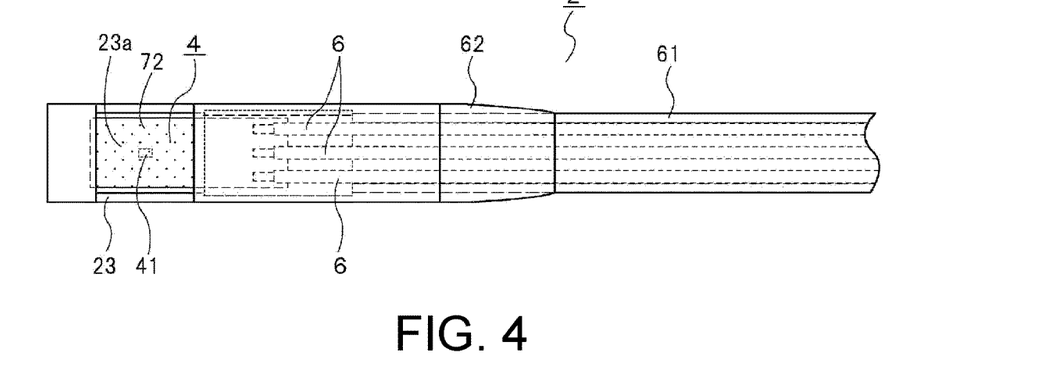
FIG. 4 is a top view in the distal end portion of the sensor device.
Figure 5:
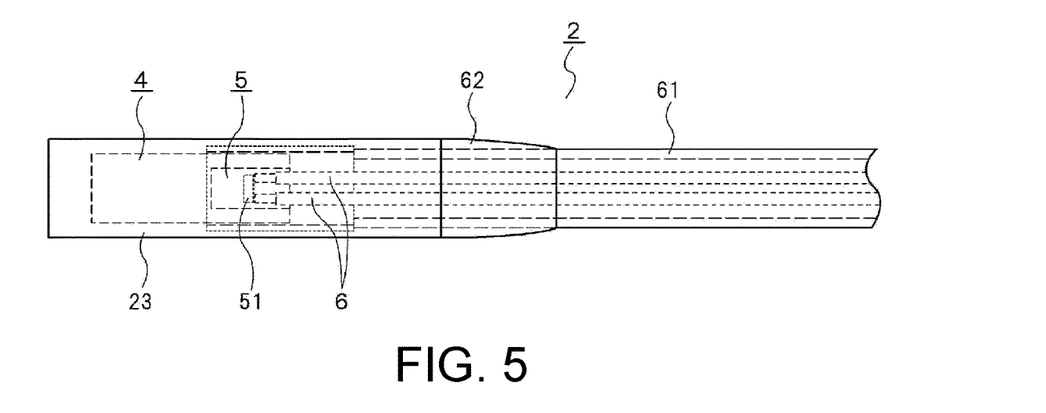
FIG. 5 is a bottom view in the distal end portion of the sensor device.
Figure 6:
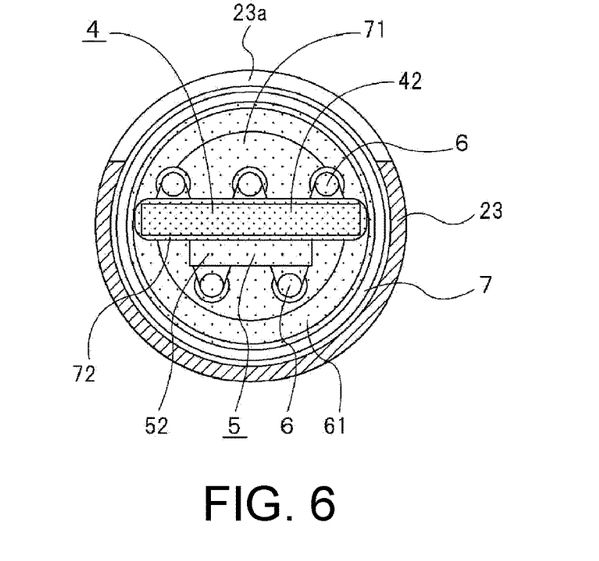
FIG. 6 is a cross-sectional view along a line Y-Y in FIG. 3.
Figure 7:
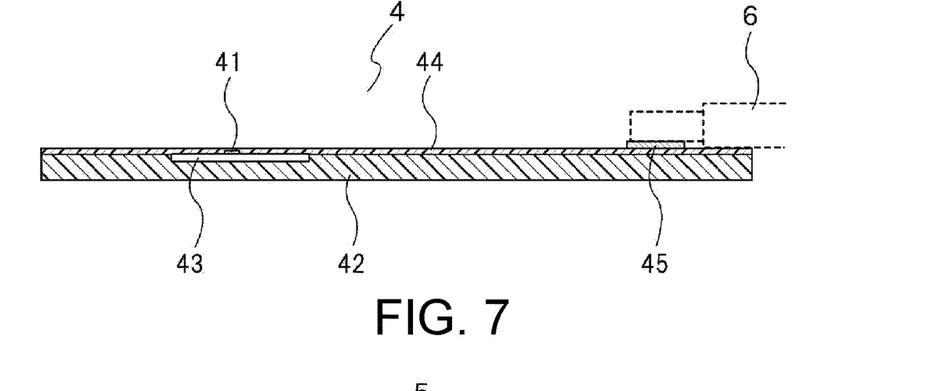
FIG. 7 is a schematic cross-sectional view illustrating a pressure sensor.
Figure 8:
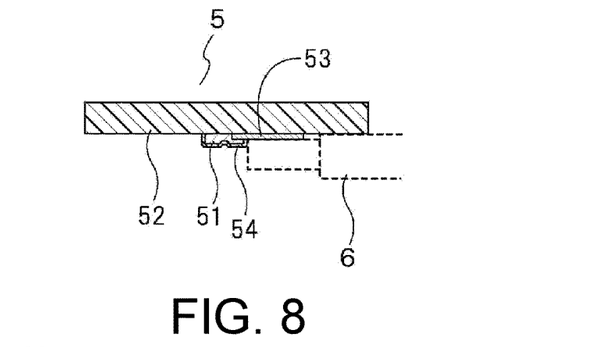
FIG. 8 is a schematic cross-sectional view illustrating a temperature sensor.
Figure 9:
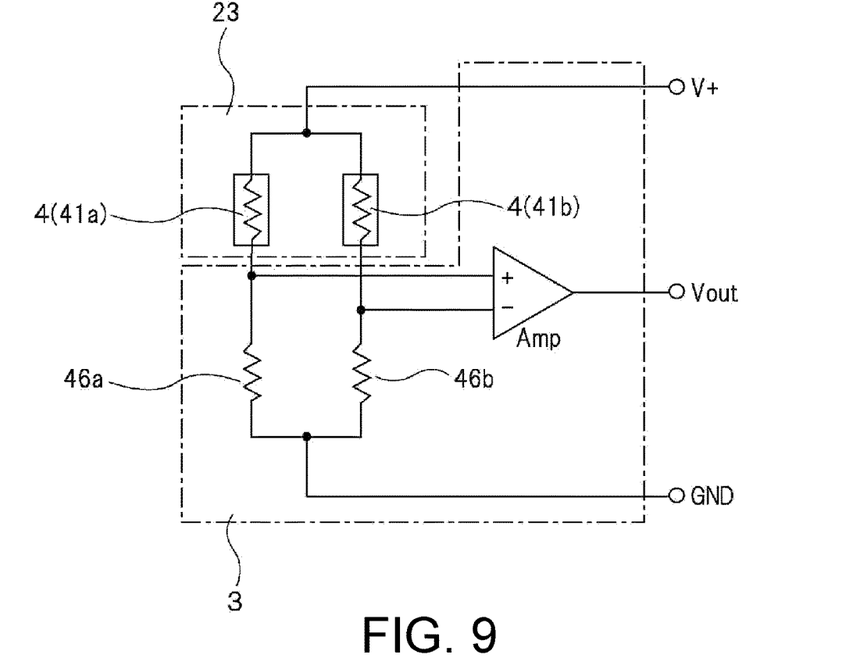
FIG. 9 is a bridge circuit diagram (half bridge circuit) illustrating a connection state of the pressure sensor.
Figure 10:
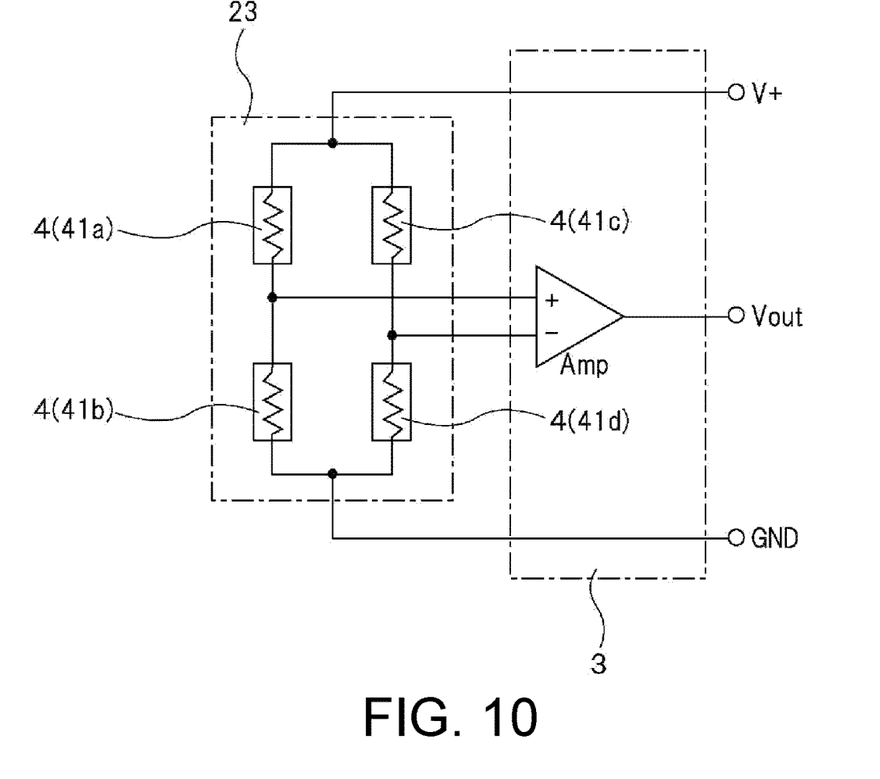
FIG. 10 is a bridge circuit diagram (full bridge circuit) illustrating a connection state of the pressure sensor.

Hereinafter, a sensor device according to an embodiment of the disclosure will be described with reference to FIGS. 1 to 10. FIG. 1 is a front view illustrating the sensor device, and FIG. 2 is a top view illustrating the sensor device. FIG. 3 is a cross-sectional view illustrating a configuration in a distal end portion of the sensor device, FIG. 4 is a top view in the distal end portion of the sensor device, and FIG. 5 is a bottom view in the distal end portion of the sensor device. In addition, FIG. 6 is a cross-sectional view along a line Y-Y in FIG. 3, and FIGS. 7 and 8 are schematic cross-sectional views illustrating a pressure sensor and a temperature sensor. FIGS. 9 and 10 are bridge circuit diagrams illustrating a connection state of the pressure sensor. Meanwhile, in the drawings, the scale of each member is appropriately changed in order to make the size of each member recognizable.

The sensor device of the present embodiment includes a pressure sensor and a temperature sensor which are made small and is configured to be suitably embedded in a catheter. The pressure sensor measures pressure in an abdominal cavity, and the temperature sensor measures a deep body temperature.

As illustrated in FIGS. 1 to 3, a sensor device 1 includes a main body portion 2 having an elongate shape and flexibility, and a connection terminal portion 3 to which the main body portion 2 is connected. The main body portion 2 includes a distal end portion 21 and a lead portion 22, and a pressure sensor 4 and a temperature sensor 5 which will be described later are disposed in the distal end portion 21. The lead portion 22 is a part in which a plurality of lead wires 6 connected to the pressure sensor 4 and the temperature sensor 5 extends. The lead wire 6 is configured such that the core wire thereof is insulated and covered, and further the plurality of lead wires 6 is insulated and covered with a resin tube 61 and are gathered as one. That is, the plurality of lead wires 6 is accommodated in the inner space of the resin tube 61. The material of the resin tube 61 is a polyimide resin.

Meanwhile, the length dimension of the main body portion 2 is approximately 1000 mm, and the distal end portion 21 and the lead portion 22 are formed to have an external diameter φ equal to or less than 1.5 mm, and preferably equal to or less than 1 mm.

The connection terminal portion 3 is a part to which leading ends of the lead wires 6 are connected, and is configured to accommodate an electronic part such as a circuit substrate in a case formed of a resin and having substantially a rectangular parallelepiped shape. Specifically, the connection terminal portion 3 is provided with detection control circuits and amplification circuits of the pressure sensor 4 and the temperature sensor 5. In addition, a USB terminal 31 is provided on one side of the connection terminal portion 3 as an input and output terminal. It is possible to monitor detection information based on outputs of the pressure sensor 4 and the temperature sensor 5 by connecting the USB terminal 31 to a control device such as a monitor.

Next, a configuration of the distal end portion 21 in the main body portion 2 in which the pressure sensor 4 and the temperature sensor 5 are disposed will be described with reference to FIGS. 3 to 8. In the distal end portion 21, a pipe-shaped distal-end-side member 23, the pressure sensor 4 and the temperature sensor 5 disposed in the inner space of the pipe-shaped distal-end-side member 23, and the plurality of lead wires 6 connected to the pressure sensor 4 and the temperature sensor 5 and led out to a rear end side is disposed.

The distal-end-side member 23 is formed of a stainless steel material in a pipe shape, and includes an opening portion 23a in the vicinity of the distal end thereof. The opening portion 23a is formed to notch a portion of a pipe-shaped outer circumference. The distal-end-side member 23 is formed to have a length dimension equal to or less than approximately 4 mm and an external diameter φ equal to or less than 1.5 mm, and preferably equal to or less than 1 mm. Therefore, the distal-end-side member is formed to have an internal diameter φ of less than at least 1.5 mm, and preferably less than 1 mm.

The pressure sensor 4 and the temperature sensor 5 are disposed in such a narrow inner space of the distal-end-side member 23. The pressure sensor 4 is a semiconductor pressure sensor, and includes a sensor element 41 having a function of a strain gauge of which the electric resistance value changes due to the displacement thereof when pressure is applied. The sensor element 41 is a piezo-resistance element, and the piezo-resistance element is formed on one surface side of a substrate 42 formed of a silicon material.

The temperature sensor 5 is a thin film thermistor, and includes a sensor element 51 of which the electric resistance value changes due to a change in temperature. The sensor element 51 is a thin film of a thermistor formed of an oxide semiconductor having a negative temperature coefficient, and the thin film of the thermistor is formed on one surface side of a substrate 52 formed of a ceramic material.

In addition, an electrode layer is formed on the substrate 42 of the pressure sensor 4 and the substrate 52 of the temperature sensor 5, and the lead wires 6 are connected to the electrode layer by soldering or welding. In a case where the lead wires 6 are bonded to the electrode layer by welding, an additional material such as solder can be omitted as compared with a case where the lead wires are bonded to the electrode layer by soldering, and thus it is possible to make a bonding portion thin.

The above-described pressure sensor 4 and temperature sensor 5 are disposed and integrated so that the other surface sides of the substrate 42 and the substrate 52 face each other. Thereby, a configuration of a sensor group including the pressure sensor 4 and the temperature sensor 5 is miniaturized. Here, the integration includes, for example, disposition according to simple butting of the other surface sides of the substrate 42 and the substrate 52 and a case according to adhesion of the other surface sides of the substrate 42 and the substrate 52. In other words, the integration is a state where the pressure sensor 4 and the temperature sensor 5 are grouped.

Specifically, the integrated pressure sensor 4 and temperature sensor 5 are formed of a polyimide resin and disposed to be inserted and fitted into the distal-end-side member 23 through a tube-shaped cover member 7. In addition, the cover member 7 is filled with an insulating material 71, and a bonding portion between the pressure sensor 4, the temperature sensor 5, and the lead wires 6 and the surroundings of the bonding portion are insulated and covered. An epoxy resin is preferably used for the insulating material 71 filled in the cover member 7, but the insulating material is not limited to the epoxy resin as long as the function thereof is satisfied.

In more detail, the formation position of the sensor element 41 in the pressure sensor 4 and the formation position of the sensor element 51 in the temperature sensor 5 deviate from each other. The substrate 42 of the pressure sensor 4 protrudes to the distal end side from the substrate 52 of the temperature sensor 5, and a region at the formation position of the sensor element 41 in the pressure sensor 4 is not covered with the insulating material 71. On the other hand, an insulating property of the region at the formation position of the sensor element 41 in the pressure sensor 4 is secured by being covered with an insulating material 72 of a silicone rubber film through silicon coating. Meanwhile, the sensor element 41 is disposed to face the opening portion 23a of the distal-end-side member 23. In addition, the resin tube 61 having the plurality of lead wires 6 gathered therein is inserted and fitted into the inner circumference on the rear end side of the distal-end-side member 23 to be fixed thereto using an adhesive 62. As the adhesive 62, for example, an epoxy resin is used.

The formation position of the sensor element 41 in the pressure sensor 4 and the formation position of the sensor element 51 in the temperature sensor 5 deviate from each other in this manner in order to avoid a likelihood that mutual detection characteristics will be affected. In addition, different materials are used as the insulating material 72 covering the region at the formation position of the sensor element 41 in the pressure sensor 4 and the insulating material 71 covering the region at the formation position of the sensor element 51 in the temperature sensor 5. This is because it is necessary to secure the insulating properties of both the pressure sensor 4 and the temperature sensor 5, and to use the insulating material 72 having flexibility in order to detect pressure in the case of the pressure sensor 4.

Further, the pressure sensor 4 and the temperature sensor 5 are provided in the cover member 7. Accordingly, in a case where the pressure sensor 4 and the temperature sensor 5 are inserted and fitted into the distal-end-side member 23, the cover member 7 can be inserted using the inner circumference of the distal-end-side member 23 as a guide, and thus an effect of facilitating an assembling process can be expected.

Next, schematic configurations of the pressure sensor 4 and the temperature sensor 5 will be described with reference to FIGS. 7 and 8. As illustrated in FIG. 7, the pressure sensor 4 is manufactured by processing a silicon semiconductor material by a micro electro mechanical system (MEMS) technique. A cavity portion 43 is formed on the silicon substrate 42, and a piezo-resistance element is formed as the sensor element 41 in a silicon layer 44 on the cavity portion 43. The piezo-resistance element is formed by applying an ion implantation method which is a semiconductor process technique for implanting impurity ions into the silicon layer 44 and implanting boron into the silicon layer 44.

In addition, a pair of (two) piezo-resistance elements are formed as the sensor element 41 in the silicon layer 44. This is to achieve high sensitivity by configuring a bridge circuit at the time of connecting the pressure sensor 4 as will be described later. Further, an electrode layer 45 is formed at each of three locations on the rear end side of the silicon substrate 42 (also see FIG. 4), and the electrode layers 45 are electrically connected to the piezo-resistance element using an internal wiring pattern not shown in the drawing. In addition, the lead wires 6 are soldered and bonded to the electrode layers 45 by welding or a so-called pulse heat method. The thickness dimension of the substrate 42 of the pressure sensor 4 is equal to or less than 100 μm, and a total thickness dimension including the electrode layers 45 is equal to or less than 150 μm.

In the pressure sensor 4, when pressure is applied to the piezo-resistance element when it operates as a diaphragm of the cavity portion 43, an electric resistance value of the piezo-resistance element changes due to the displacement thereof, and the pressure sensor 4 processes the change with an electronic circuit to detect pressure.

As illustrated in FIG. 8, the temperature sensor 5 is a surface mounting type, and includes the substrate 52, an electrode layer 53, a heat-sensitive film serving as the sensor element 51, and a protection film 54. The temperature sensor 5 is a thin film thermistor, and a total thickness dimension thereof is equal to or less than 100 μm.

The substrate 52 is formed using a ceramic material such as insulating zirconia, silicon nitride, alumina, or a mixture including at least one of them. The substrate 52 is formed to be thin and have a thickness dimension of equal to or less than 100 μm, and preferably 10 μm to 80 μm. In addition, a bending strength of the substrate 52 is equal to or higher than 690 MPa, and an average particle diameter of the ceramic material after burning is 0.1 μm to 2 μm. By setting the range of an average particle diameter in this manner, it is possible to secure a bending strength of equal to or higher than 690 MPa and suppress cracking during the manufacture of the thinned substrate 52. In addition, because the substrate 52 has a small thickness dimension, it is possible to reduce a thermal capacity.

A pair of electrode layers 53 are formed on the substrate 52 as portions to which a heat-sensitive film is electrically connected. Each of the pair of electrode layers 53 is formed by forming a metal thin film having a thickness dimension of equal to or less than 1 μm by a thin film forming technique such as a sputtering method, and noble metals such as gold (Au), silver (Ag), copper (Cu), platinum (Pt), and palladium (Pd) and alloys thereof, for example, an Ag—Pd alloy, are applied as the metal material.

Meanwhile, the pair of electrode layers 53 are portions to which the lead wires 6 are bonded by welding, and an alloy containing gold (Au: a melting point of 1064° C.), silver (Ag: 961° C.), copper (Cu: 1085° C.), or at least one of them as a main component is preferably used as a low melting point metal. In addition, although the electrode layer 53 is formed under the heat-sensitive film in the present embodiment, the electrode layer may be formed over or within the heat-sensitive film.

The heat-sensitive film is a heat-sensitive thin film and a thin film of a thermistor. The heat-sensitive film is formed on the electrode layer 53 by a thin film forming technique such as a sputtering method to be electrically connected to the electrode layer 53.

The protection film 54 covers a region in which the heat-sensitive film is formed and covers the electrode layer 53 formed such that at least a portion of the electrode layer 53 is exposed. The protection film 54 can be formed by forming a film of silicon dioxide, silicon nitride, or the like by a thin film forming technique such as a sputtering method, or can be formed by forming lead glass, borosilicate glass, lead borosilicate glass, or the like by a printing method.

Meanwhile, the lead wire 6 is formed of a low melting point metal, that is, a metal having a melting point of equal to or less than 1300° C., and a copper alloy containing copper, such as phosphor bronze, constantan, or manganin, is used as a main component.

In a case where the electrode layer 53 of the temperature sensor 5 and the lead wires 6 are bonded to each other by, for example, laser welding, a melting point of the lead wire 6 is equal to or less than 1300° C., and thus the melting point is not set to a temperature of equal to or higher than 1300° C. even when the lead wire is melted by heating using a laser beam or the like. Therefore, the melting point does not exceed a melting point of 1600° C. to 2100° C. of the ceramic substrate 52, and thus it is possible to bond the lead wires 6 by suppressing the damage of the electrode layer 53 of the temperature sensor 5 and the substrate 52 immediately below the electrode layer 53. Further, in this case, an additional material such as a bump is not used. Accordingly, the lead wires are not bonded in a state where an additional material is substantially added to a connection (bonding) portion, and a thermal capacity is not increased, so that it is possible to increase the speed of thermal responsiveness.

Hitherto, iron-based metals such as stainless steel, Kovar, and a nickel alloy have been used for the above-described lead wire. Iron-based metals have high melting points. For example, both stainless steel and Kovar are iron-based alloys, and thus the temperatures thereof may rise to approximately 1538° C. which is a melting point of iron. When a lead wire of such a high melting point metal is irradiated with a laser beam for laser welding, the lead wire and the surroundings thereof are heated to a high temperature, which results in a problem that an insulating substrate (for example, an alumina substrate) is likely to be damaged. According to the configuration of the present embodiment, such a problem can be solved.

In the temperature sensor 5, an electric resistance value changes due to a change in temperature, and the temperature sensor processes the change with an electronic circuit to detect temperature.

On the other hand, wearable equipment monitoring biological information and equipment used in a catheter, which is medical equipment, and the like needs to be formed of a material taking biocompatibility into consideration for a material to be used in a case where there is a high risk of the equipment being exposed inside of a living body. In the present embodiment, a stainless steel material is used for the distal-end-side member 23, the substrate 42 formed of a silicon material is used for the pressure sensor 4, the substrate 42 formed of a ceramic material is used for the temperature sensor 5, a polyimide resin material is used for the cover member 7, an epoxy resin is used for the insulating material 71 in the cover member 7, a polyimide resin is used for the resin tube 61, and a silicone rubber material is used for the coating of the pressure sensor 4. It is confirmed that these materials have biocompatibility, and thus safety can be secured.

Next, a connection state of the pressure sensor will be described with reference to FIGS. 9 and 10. As illustrated in FIG. 9, the pressure sensor 4 is bridge-connected to a power supply $V_+$, thereby configuring a bridge circuit. Specifically, the bridge circuit is a half bridge circuit, and a series circuit of a sensor element 41a and a reference resistor 46a of the pressure sensor 4 and a series circuit of a sensor element 41b and a reference resistor 46b are connected to the power supply $V_+$ in parallel. In addition, an output terminal is connected in the middle of each of the series circuits, and the output terminal is connected to an amplifier Amp to be able to detect a differential output as an output voltage Vout. Therefore, it is also possible to detect a signal of a minute change in pressure.

In such a connection state, the sensor element 41a and the sensor element 41b of the pressure sensor 4 are disposed in the distal-end-side member 23, and the reference resistors 46a and 46b and the amplifier Amp are accommodated in the connection terminal portion 3.

FIG. 10 illustrates a case where a bridge circuit is configured as a full bridge circuit. Four sensor elements of the pressure sensor 4 are provided, and a series circuit of sensor elements 41a and 41b and a series circuit of sensor elements 41c and 41d are connected to a power supply $V_+$ in parallel. Thus, it is possible to perform detection with higher sensitivity.

In such a connection state, the sensor elements 41a, 41b, 41c, and 41d of the pressure sensor 4 are disposed in the distal-end-side member 23, and the amplifier Amp is accommodated in the connection terminal portion 3.

Meanwhile, it is also preferable that a bridge circuit be configured for the connection of the temperature sensor 5. In this case, although not shown in the drawing, for example, a series circuit of the sensor element 51 for detection and a resistor for detection and a series circuit of a sensor element for compensation and a resistor for compensation are connected to a power supply $V_+$ in parallel. In addition, an output terminal is connected in the middle of each of the series circuits, and the output terminal is connected to an amplifier Amp to detect a differential output as an output voltage Vout. With such a configuration, it is also possible to detect a signal of a minute change in temperature.

Figure 11:
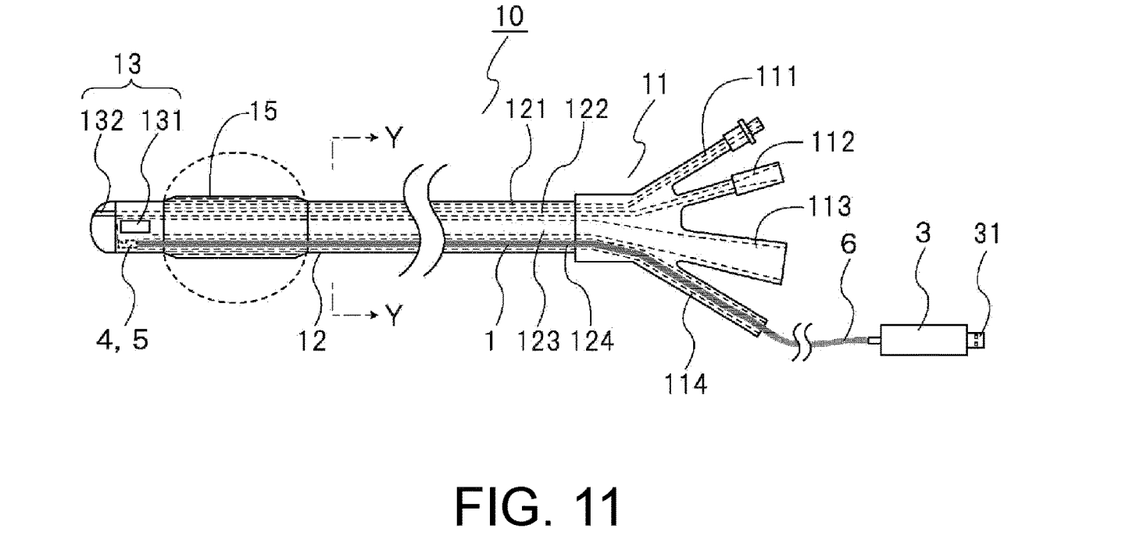
FIG. 11 is a front view illustrating a state where the sensor device is embedded in a urethra catheter.
Figure 13:
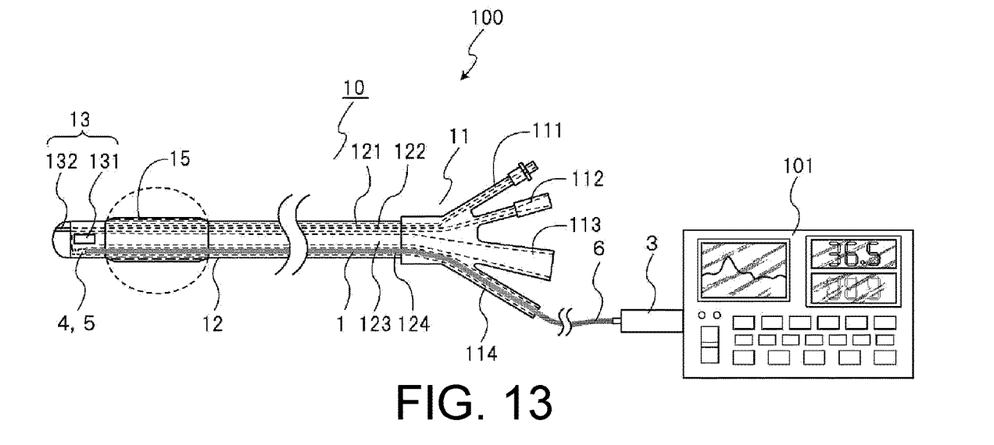
FIG. 13 is a front view illustrating a system including the sensor device.
Figure 14:
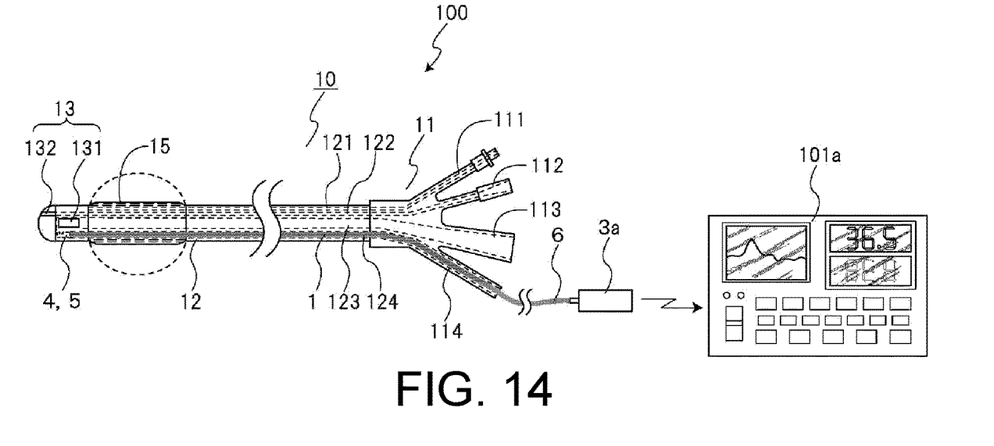
FIG. 14 is a front view illustrating a system including the sensor device.

Next, a catheter in which the above-described sensor device 1 is embedded and a system including the sensor device 1 will be described with reference to FIGS. 11 to 14. FIG. 11 is a front view illustrating a state where a sensor device is embedded in a urethra catheter, FIG. 12 is a cross-sectional view along a line Y-Y in FIG. 11, and FIGS. 13 and 14 illustrate a system including the sensor device.

The catheter of the present embodiment is a urethra catheter. The urethra catheter is used for the purpose of continuously discharging urine by being inserted into a patient's bladder from the urethra, and the urethra catheter is provided with a balloon and used by placing its distal end portion in the bladder.

Figure 12:
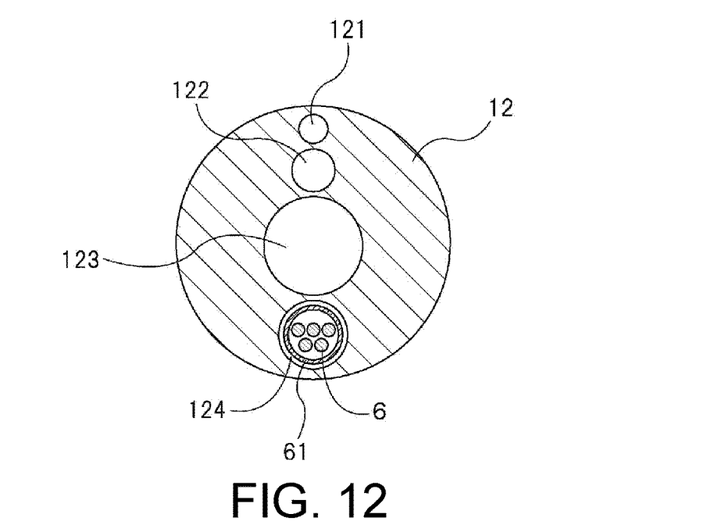
FIG. 12 is a cross-sectional view along a line Y-Y in FIG. 11.

As illustrated in FIGS. 11 and 12, a urethra catheter 10 includes a base portion 11 and a shaft 12 continuously extending from the base portion 11. The catheter 10 is, for example, a 4-way type and has a total length of approximately 250 mm to 430 mm. The base portion 11 is provided with a balloon funnel 111, a washing water funnel 112, a urination funnel 113, and a sensor funnel 114.

Four lumens are formed in the shaft 12 corresponding to each the funnels 111, 112, 113, and 114, and the shaft 12 has appropriate rigidity and flexibility. Further, in the distal end portion 13 of the shaft 12, the pressure sensor 4 and the temperature sensor of the sensor device 1 are disposed, and a urination hole 131 and a washing water outflow hole 132 are formed. Further, a balloon 15 is provided near the rear end of the distal end portion 13 of the shaft 12.

A syringe is connected to the balloon funnel 111, and air or sterilized water is injected into the balloon funnel to inflate the balloon 15. The syringe is connected to the washing water funnel 112 as necessary, so that washing water is supplied into the bladder to wash the inside of the bladder. A urine collection bag is connected to the urination funnel 113, so that urine in the bladder is discharged from the body and stored in the urine collection bag. The lead wires 6 of the pressure sensor 4 and the temperature sensor 5 disposed at the distal end portion 13 of the shaft 12 are led out from the sensor funnel 114.

Among the four lumens, a first lumen 121 serves as a flow path through which air sent from the balloon funnel 111 passes, and the first lumen is connected to the balloon 15, so that the balloon 15 is inflated with air sent through the first lumen 121. A second lumen 122 serves as a flow path through which washing water sent from the washing water funnel 112 passes, and the second lumen is connected to the washing water outflow hole 132, so that washing water sent through the second lumen 122 flows out of the washing water outflow hole 132. A third lumen 123 is connected to the urination hole 131 to serve as a flow path through which urine flowing out of the patient's bladder passes.

A fourth lumen 124 is a portion into which the lead wires 6 of the pressure sensor 4 and the temperature sensor 5 are inserted, the pressure sensor 4 and the temperature sensor are disposed at the distal end portion 13 of the shaft 12, and the lead wires 6 pass through the fourth lumen 124, so that the connection terminal portion 3 is led out to the outside. In this manner, the sensor device 1 is embedded in the catheter 10.

Meanwhile, the external diameter dimension of the shaft 12 is approximately 12 to 24 French, and a synthetic resin such as polyurethane, polyolefin, polyamide, polyether polyamide, or silicone rubber can be used as the material constituting the shaft 12.

FIG. 13 illustrates a system including a sensor device. The system 100 includes the catheter 10 having the sensor device 1 embedded therein, and a control device 101. The control device 101, which is a monitor conforming to the YSI-400 standard, includes a display portion and is configured with a CPU including a computation unit and a control unit, a ROM and a RAM, which are storage means, and a microcomputer including input and output control means mounted, and a USB terminal 31 of the connection terminal portion 3 in the sensor device 1 can be connected thereto. Thus, it is possible to display biological information including bladder internal pressure and body temperature by connecting the sensor device 1 to the control device 101.

FIG. 14 illustrates a configuration in which a sensor device and a control device having the sensor device connected thereto are connected to each other through a wireless line. A control device 101a is provided with a wireless transmission and reception unit, and a connection terminal portion 3a is provided with a wireless module and a built-in battery. Thus, it is possible to transmit biological information from the connection terminal portion 3a to the control device 101a in a wireless manner and to display the biological information on the control device 101a.

For this reason, the sensor device 1 and the control device 101a are connected to each other in a wireless manner, and thus lead lines and the like are not obstructed during an operation, which leads to an advantage in that handling is facilitated.

Next, a case where a patient is treated with the urethra catheter 10 will be described. A urine collection bag is connected to the urination funnel 113, and the catheter 10 is inserted from the patient's urethral meatus. After it is confirmed that the balloon 15 has reached the inside of the bladder and urine has flowed to the catheter 10, a syringe is connected to the balloon funnel 111, and air or sterilized water is injected into the balloon 15 to inflate the balloon 15. The catheter 10 is pulled out until the balloon comes into contact with the bladder neck, and the distal end portion 13 of the catheter 10 is placed in the bladder. Then, the USB terminal 31 of the connection terminal portion 3 is connected to the control device 101. Urine is continuously discharged from the body in this manner and stored in the urine collection bag.

Specifically, urine in the bladder flows from the urination hole 131 to the third lumen 123 and reaches the urine collection bag. In addition, since the pressure sensor 4 and the temperature sensor 5 which are disposed at the distal end portion 13 of the shaft 12 of the sensor device 1 are placed in the bladder, a bladder internal pressure is measured by the pressure sensor 4, a deep body temperature is measured by the temperature sensor 5, and detection signals thereof are transmitted to the control device 101. In this case, the detection of pressure in the bladder by the pressure sensor 4 is performed with high accuracy through urine flowing from the urination hole 131 because the opening portion 23a of the distal-end-side member 23 faces the pressure sensor 4. A bladder internal pressure and a deep body temperature are displayed in the control device 101 in this manner, and thus it is possible to monitor biological information.

Further, the inside of the bladder is washed by connecting a syringe to the washing water funnel 112 and making washing water flow from the washing water outflow hole 132 into the bladder, as necessary.

As described above, according to the present embodiment, it is possible to provide the sensor device 1 that can be made small and to realize a catheter that can reduce a burden on a patient.

Meanwhile, the sensor device of the disclosure is preferably used for a catheter, but is not limited thereto. The sensor device can also be applied to other medical equipment. Further, in addition to the field of medical equipment, the application of the sensor device to equipment and a device which include a pressure sensor and a temperature sensor and need to be miniaturized is not precluded.

The disclosure is not limited to the configuration of the above-described embodiment, and various modifications can be made without departing from the scope of the invention. In addition, the above-described embodiment is presented as an example and is not intended to limit the scope of the invention. The novel embodiment may be embodied in various other modes, and may include various omissions, substitutions, and modifications. The embodiment and modification thereof are within the scope and the gist of the invention, and are within the scope of the invention described in the scope of claims and the equivalent thereof.

What is claimed is:

1. A sensor device, that has a distal end side and a rear end side, comprising:
    a tubular distal-end-side member disposed on the distal end side of the sensor device;
    a pressure sensor and a temperature sensor which are integrated and accommodated in an inner space inside a tube of the distal-end-side member; and
    at least one lead wire which is connected to the pressure sensor and the temperature sensor and is led out to the rear end side of the sensor device,
    wherein the pressure sensor comprises a first sensor element and a first substrate having a first surface side and a second surface side opposite to the first surface side, wherein the first sensor element is disposed on the first surface side of the first substrate,
    the temperature sensor comprises a second sensor element and a second substrate having a third surface side and a fourth surface side opposite to the third surface side, wherein the second sensor element is disposed on the third surface side of the second substrate, the pressure sensor and the temperature sensor are disposed and integrated so that the second surface side of the first substrate and the fourth surface side of the second substrate face each other, and when viewed along an axial direction of the tubular distal-end-side member, the integrated structure of the pressure sensor and the temperature sensor overlaps with the center of the tubular distal-end-side member.

2. The sensor device according to claim 1, wherein a position of the first sensor element in the pressure sensor and a position of the second sensor element in the temperature sensor deviate from each other.

3. The sensor device according to claim 1, wherein the pressure sensor is manufactured with a semiconductor material, and the temperature sensor is a thin film thermistor.

4. The sensor device according to claim 1, wherein an internal diameter of the distal-end-side member is less than 1 mm.

5. The sensor device according to claim 1, wherein a leading end of the lead wire is connected to a connection terminal including an input and output terminal.

6. The sensor device according to claim 1, wherein the pressure sensor and the temperature sensor are accommodated in the inner space of the distal-end-side member through a tube-shaped cover member.

7. The sensor device according to claim 1, wherein the at least one lead wire comprises a plurality of lead wires, the number of the plurality of lead wires is two or more, and the plurality of lead wires are gathered as one by a resin tube and are insulated and covered.

8. The sensor device according to claim 1, wherein the pressure sensor is configured to measure a pressure in an abdominal cavity, and the temperature sensor is configured to measure a deep body temperature.

9. The sensor device according to claim 1, wherein a material having biocompatibility is used for the distal-end-side member, the first substrate and the second substrate respectively included in the pressure sensor and the temperature sensor, and an insulating material covering the pressure sensor and the temperature sensor.

10. A catheter comprising the sensor device according to claim 1.

11. The sensor device according to claim 1, wherein the pressure sensor is bridge-connected to configure a circuit as a bridge circuit.

12. The sensor device according to claim 11, wherein an amplifier is connected to an output end of the bridge circuit.

13. A system comprising:
the sensor device according to claim 1; and
a control device to which the sensor device is connected.

14. The system according to claim 13, wherein
the sensor device and the control device are connected to each other through a wireless line.

* * * * *